(12) United States Patent
Simon et al.

(10) Patent No.: US 9,205,119 B2
(45) Date of Patent: Dec. 8, 2015

(54) NEUROPROTECTIVE COMPOSITIONS AND METHODS

(75) Inventors: James E. Simon, Princeton, NJ (US); Qing-li Wu, Annandale, NJ (US); Wenbin Deng, Davis, CA (US)

(73) Assignees: Rutgers, The State University of New Jersey, New Brunswick, NJ (US); The Regents of the University of California, Oakland, CA (US)

( * ) Notice: Subject to any disclaimer, the term of this patent is extended or adjusted under 35 U.S.C. 154(b) by 716 days.

(21) Appl. No.: 13/260,475

(22) PCT Filed: Mar. 26, 2010

(86) PCT No.: PCT/US2010/028815
§ 371 (c)(1),
(2), (4) Date: Feb. 14, 2012

(87) PCT Pub. No.: WO2010/111584
PCT Pub. Date: Sep. 30, 2010

(65) Prior Publication Data
US 2012/0136047 A1    May 31, 2012

Related U.S. Application Data

(60) Provisional application No. 61/163,615, filed on Mar. 26, 2009.

(51) Int. Cl.
| | |
|---|---|
| *A61K 36/185* | (2006.01) |
| *A61K 31/196* | (2006.01) |
| *A61K 31/355* | (2006.01) |
| *C07C 69/017* | (2006.01) |
| *C07D 311/70* | (2006.01) |

(52) U.S. Cl.
CPC ............ *A61K 36/185* (2013.01); *A61K 31/196* (2013.01); *A61K 31/355* (2013.01); *C07C 69/017* (2013.01); *C07D 311/70* (2013.01); *A61K 2236/35* (2013.01)

(58) Field of Classification Search
CPC .............. A61K 31/355; A61K 36/185; A61K 2236/35; C07D 311/70; C07C 69/017
USPC ............ 549/410, 407; 514/548, 456; 560/193
See application file for complete search history.

(56) References Cited

U.S. PATENT DOCUMENTS

| | | | |
|---|---|---|---|
| 2,423,545 A | 7/1947 | Aeschback et al. | |
| 6,173,512 B1 | 1/2001 | Bitelli | |
| 7,371,413 B2 * | 5/2008 | Simon et al. | 424/725 |
| 2003/0129294 A1 | 7/2003 | Barclay et al. | |

OTHER PUBLICATIONS

Krishnamurthy, R., "Sargahydroquinoic acid and its acetylated derivative are novel neuroprotective agents against injury induced by focal cerebral ischemia", 2008, Abstracts of the Annual Meeting of the Society for Neuroscience, Society for Neuroscience, Washington, DC, 38, p. 1-2.*
Céspedes, C. L., "Insect growth inhibition by tocotrienols and hydroquinones from< i> Roldana barba-johannis</i>." Phytochemistry 65.13 (2004): 1963-1975.*
Lee, H., "Protective effect of green tea polyphenol EGCG against neuronal damage and brain edema after unilateral cerebral ischemia in gerbils." Journal of neuroscience research 77.6 (2004): 892-900.*
Durukan, A.,"Acute ischemic stroke: overview of major experimental rodent models, pathophysiology, and therapy of focal cerebral ischemia." Pharmacology Biochemistry and Behavior 87.1 (2007): 179-197.*
Wook et al., "Anticholinesterase activity of plastoquinones from Sargassum sagamianum: lead compounds for alzheimer's disease therapy," Phytotherapy Research (Jan. 1, 2007); 21(5):423-426.
Kusumi et al., "Structures of New Plastaoquinones from the Brown Alga Sargassum Serratifolium," Published by the Chemical Society of japan (Jan. 1, 1979).

* cited by examiner

*Primary Examiner* — Samantha Shterengarts
*Assistant Examiner* — Matt Mauro
(74) *Attorney, Agent, or Firm* — Fox Rothschild LLP; Gerard P. Norton; Wansheng Jerry Liu (57) ABSTRACT

This disclosure concerns novel methods for preventing or treating neurological or neurodegenerative diseases or disorders by using *kombo* butter acid enriched extracts derived from the seeds of African nutmeg, the main active compounds isolated from the extracts, namely sargaquinoic acid, sargachromenol, and sargahydroquinoic acid, or synthetic analogs or derivatives thereof, as neuroprotective agents. The methods for preparing the *kombo* butter or *kombo* butter acid extracts and the methods for isolating and purifying the active compounds and for preparing their acetylated derivatives are also described.

15 Claims, 4 Drawing Sheets

NEUROPROTECTIVE COMPOSITIONS AND METHODS

CROSS REFERENCE TO RELATED APPLICATIONS

This application is a U.S. National Stage Application of International Application No. PCT/US2010/028815, filed on Mar. 26, 2010, which claims the benefit under 35 U.S.C. §119(e) of U.S. Provisional Application No. 61/163,615, filed on Mar. 26, 2009, both of which are incorporated herein by reference.

STATEMENT REGARDING FEDERALLY FUNDED RESEARCH

This invention was made with government support by the National Institutes of Health, Grant No. NS059043. The U.S. Government has certain rights in this invention.

FIELD OF THE INVENTION

The present invention relates to the prevention and treatment of neurological diseases or disorders by using *kombo* butter acid enriched extracts, the main active compounds isolated from the extracts, or synthetic analogs or derivatives thereof. The methods for preparation of *kombo* butter or *kombo* butter acid extracts and the methods for isolation and purification of the main active compounds and for preparation of their derivatives are also described.

BACKGROUND OF THE INVENTION

Neuroprotection is the mechanism and strategy used to protect against neuronal injury or degeneration in the CNS following acute disorders (e.g., stroke or nervous system injury/trauma) or as a result of chronic neurodegenerative diseases (e.g., Parkinson's, Alzheimer's, multiple sclerosis). The goal of neuroprotection is to limit neuronal dysfunction/death after CNS injury and attempt to maintain the highest possible integrity of cellular interactions in the brain resulting in an undisturbed neural function.

There are a wide range of neuroprotective products available or under investigation and some products can potentially be used in more than one disorder, as many of the underlying mechanisms of damage to neural tissues (in both acute disorders and in chronic neurodegenerative diseases) are similar. Products with neuroprotective effects are grouped into the following categories: free radical trappers/scavengers, anti-excitotoxic agents, apoptosis (programmed cell death) inhibitors, anti-inflammatory agents, neurotrophic factors, metal ion chelators, ion channel modulators and gene therapy.

Stroke is the rapidly developing loss of brain functions due to a disturbance in the blood vessels supplying blood to the brain, which can be due to ischemia (lack of blood supply) caused by thrombosis or embolism, or due to a hemorrhage. Stroke is the second most common cause of death and major contributor to serious physical, emotional, and cognitive deficits worldwide. (Donnan, G. A., et al., *Lancet*, 371(9624): 1612-23 (May 2008)). The National Stroke Association states that stroke is the number one cause of adult disability in America (66% of survivors having some type of disability)—there are an estimated 15 million strokes occurring worldwide each year. Stroke is a medical emergency and can cause permanent neurological damage, complications and death if not promptly diagnosed and treated.

Ischemic stroke is the most common type, accounting for about 87% of all strokes. Rapid deprivation of oxygen and glucose to brain induces over-activation of glutamate receptors, accumulation of intracellular $Ca^{2+}$, abnormal recruitment of inflammatory cells, excessive production of free radicals, leading to the spread of ischemic neuronal death. (Mehta, S. L., et al., *Brain Res. Rev.* 54(1):34-66 (2007); Durukan, A. and Tatlisumak T., *Pharmacol. Biochem. Behav.* 87(1):179-97 (2007)). Several neuroprotective agents designed to block these pathological events have been evaluated in preclinical stroke models. (Green, A. R., *Br. J. Pharmacol.*, 153 Suppl. 1:S325-38 (2008)). However, translation of neuroprotective benefits from the laboratory bench to the emergency room has not been successful and thrombolytic therapy remains the only FDA approved acute therapy for ischemic stroke, which benefits only about 2-5% of all hospitalized stroke patients. Therefore, the need to identify safe and efficient neuroprotective agents that will benefit a larger number of acute stroke patients remains vitally important.

SUMMARY OF THE INVENTION

The present invention provides compositions and methods to fulfill the forgoing need by describing the use of *kombo* butter acid enriched extracts and their main active components or synthetic analogs as useful neuroprotective agents for the prevention or treatment of neurological or neurodegenerative diseases or disorders. The *kombo* butter acid enriched extracts are derived from the seeds of *Pycnanthus angolensis* Warb. (*P. Kombo*) (sometimes incorrectly spelled in the literature as *Pycnanthus anglensis, Pycnanthus anglonensis* but all referring to this same genus and species), which is also commonly known as African nutmeg, and their main active components include sargaquinoic acid (KB-1), sargachromenol (KB-2), and sargahydroquinoic acid (KB-3). This invention provides methods of modifying central nervous system (CNS) injury using *kombo* butter, *kombo* butter acid extracts and/or the above-named main active components or derivatives thereof. The invention also provides the use of sargahydroquinoic acid (KB-3) and the acetylated derivative of 1,4-diacetylsargahydroquinoic acid (KB-3a) as neuroprotective agents in treatment of ischemic stroke using the focal cerebral ischemia model of permanent middle cerebral artery occlusion (pMCAO).

Specifically, in the first aspect the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III):

(I)

(II)

(III)

or a pharmaceutically acceptable salt, solvate, or prodrug thereof as a neuroprotective agent, wherein:

$R^1$, at each occurrence, is independently hydrogen or $C_{1-6}$ alkyl;

$R^2$, $R^3$, and $R^4$ are each independently hydrogen or $R^5C(O)$—;

$R^5$ is selected from $C_{1-6}$ alkyl, $C_{6-10}$ aryl, or 5- to 10-membered heteroaryl, wherein the alkyl is optionally substituted by one, two, or three substituents independently selected from hydroxyl, halo, $C_{1-4}$ alkoxy, and —$CO_2R^6$, and wherein the aryl or heteroaryl is each optionally substituted by one to five substituents independently selected from $C_{1-4}$ alkyl, hydroxyl, halo, $C_{1-4}$ alkoxy, and —$CO_2R^6$; and $R^6$ is hydrogen or $C_{1-4}$ alkyl.

In a second aspect the present invention provides a method for preventing or treating a neurological or neurodegenerative disease or disorder, the method comprising administering to a subject suffering from the disease or disorder a composition comprising a chemical fraction of African nutmeg seeds. More specifically, the chemical fraction of African nutmeg seeds is a *kombo* butter acid extract, for which the method of preparation is also described.

In a third aspect the present invention provides a compound of Formula (KB-2a), namely 6-acetyl-sargachromenal, or (KB-3a), namely 1,4-diacetyl-sargahydroquinoic acid:

these active compounds, and for enhancing the compound stability are also described. These products will be useful for preventing or treating a wide range of neurological or neurodegenerative diseases and disorders, such as those related to neuropathology, cognitive memory and cognitive deterioration, including but not limited to ischemic stroke.

BRIEF DESCRIPTION OF THE DRAWINGS

FIG. 4 depicts the effect of KB-3a treatment on neurological function following pMCAO. Vehicle or 30 mg/kg KB-3a was administered 2 hr before and 6 hr after-pMCAO. (A) Neurological deficits were evaluated before and 24 hr post-ischemia on an 18-point based scale. (See Garcia, J. H., et al., *Stroke*, 26:627-34 (1995)). Histogram values represent or a pharmaceutically acceptable salt, solvent or prodrug thereof. The invention also encompasses a composition comprising either of these compounds and use of the compounds or compositions as neuroprotective agents for preventing or treating neurological or neurodegenerative disease or disorders.

In addition, the methods for producing *kombo* butter and *kombo* butter acid extracts, for isolating and purifying the three main active compounds, for preparing derivatives of mean±SEM. (B) Percentage right-biased swing (elevated body swing test) (*, $p<0.01$; **, $p<0.02$).

DETAILED DESCRIPTION OF THE INVENTION

The present invention relates to the potential healthcare products and applications arising from our discovery that *kombo* butter, derived from the seeds of *Pycnanthus angolensis* Warb. (*P. Kombo*), commonly known as African nutmeg, as well as *kombo* butter acid extract and each of three major pure compounds from *kombo*, namely, sargaquinoic acid (KB-1), sargachromenol (KB-2), and sargahydroquinoic acid (KB-3), and the derivatives thereof, possess significant neuroprotective activity. We have determined that the adult pMCAO mice (permanent middle cerebral artery occlusion) treated with the preparations and compounds showed significant reduction in the brain infarct volume and neuronal damage compared with the vehicle-treated control group. To determine whether the induced reduction in infarct volume could translate into functional recovery, neurological evaluations were performed. The results showed that the mice treated with the preparations and compounds exhibited a significant improvement in neurological performance. Finally, we also describe the protocols to prepare the bioactive reparations including *kombo* butter acid extract, which is enriched in KB-1, KB-2 and KB-3, and the derivatives, and purify the major compounds of sargaquinoic acid (KB-1), sargachromenol (KB-2), and sargahydroquinoic acid (KB-3), and the derivatives thereof in high yield either from *kombo* butter or directly from African nutmeg seeds.

In the first aspect the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III):

or a pharmaceutically acceptable salt, solvate, or prodrug thereof as a neuroprotective agent.

In one embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein:

$R^1$, at each occurrence, is independently hydrogen or $C_{1-6}$ alkyl;

$R^2$, $R^3$, and $R^4$ are each independently hydrogen or $R^5C(O)$—;

$R^5$ is selected from $C_{1-6}$ alkyl, $C_{6-10}$ aryl, or 5- to 10-membered heteroaryl, wherein the alkyl is optionally substituted by one, two, or three substituents independently selected from hydroxyl, halo, $C_{1-4}$ alkoxy, and —$CO_2R^6$, and wherein the aryl or heteroaryl is each optionally substituted by one to five substituents independently selected from $C_{1-4}$ alkyl, hydroxyl, halo, $C_{1-4}$ alkoxy, and —$CO_2R^6$; and $R^6$ is hydrogen or $C_{1-4}$ alkyl.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein:

$R^1$, at each occurrence, is independently hydrogen or $C_{1-6}$ alkyl;

$R^2$, $R^3$, and $R^4$ are each independently hydrogen or $R^5C(O)$—; and $R^5$ is $C_{1-4}$ alkyl, $HO_2CCH_2CH_2$—, phenyl, or 3-pyridinyl.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein $R^1$ is each hydrogen and $R^2$, $R^3$, and $R^4$ are each $CH_3C(O)$—.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein $R^1$, $R^2$, $R^3$, and $R^4$ are each a hydrogen atom and wherein Formulas (I), (II), and (III) represent sargaquinoic acid (KB-1), sargachromenol (KB-2), and sargahydroquinoic acid (KB-3), respectively.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound selected from sargaquinoic acid (KB-1), sargachromenol (KB-2), and sargahydroquinoic acid (KB-3), or a pharmaceutically acceptable salt, solvate, or prodrug thereof, wherein the compound is isolated from a chemical fraction of African nutmeg seeds.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound selected from sargaquinoic acid (KB-1), sargachromenol (KB-2), and sargahydroquinoic acid (KB-3), or a pharmaceutically acceptable salt, solvate, or prodrug thereof, wherein the compound is a component of a chemical fraction of African nutmeg seeds.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound selected from sargaquinoic acid (KB-1), sargachromenol (KB-2), and sargahydroquinoic acid (KB-3), or a pharmaceutically acceptable salt, solvate, or prodrug thereof, wherein the compound is isolated from or a component of a chemical fraction of African nutmeg seeds, wherein the chemical fraction of African nutmeg seeds is a *kombo* butter acid extract prepared by a process comprising the steps of:
  (i) optionally milling the African nutmeg seeds to obtain a ground seed paste;
  (ii) extracting the African nutmeg seeds or the ground seed paste with an aqueous basic solution to obtain a solution of *kombo* butter acid salts and a residue;
  (iii) acidifying the solution of *kombo* butter acid salts to obtain a mixture of *kombo* butter acids;
  (iv) extracting the mixture of *kombo* butter acids with a non-polar organic solvent to obtain an aqueous fraction and an organic fraction; and
  (v) evaporating the solvent from the organic fraction to obtain the *kombo* butter acid extract.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound selected from sargaquinoic acid (KB-1), sargachromenol (KB-2), and sargahydroquinoic acid (KB-3), or a pharmaceutically acceptable salt, solvate, or prodrug thereof, wherein the compound is isolated from or a component of a chemical fraction of African nutmeg seeds, wherein the chemical fraction of African nutmeg seeds is a *kombo* butter acid extract prepared by a process comprising the steps of:
  (i) optionally milling the African nutmeg seeds to obtain a ground seed paste;
  (ii) extracting the African nutmeg seeds or the ground seed paste with an aqueous basic solution to obtain a solution of *kombo* butter acid salts and a residue;
  (iii) acidifying the solution of *kombo* butter acid salts to obtain a mixture of *kombo* butter acids;
  (iv) extracting the mixture of *kombo* butter acids with a non-polar organic solvent to obtain an aqueous fraction and an organic fraction;
  (v) evaporating the solvent from the organic fraction to obtain the *kombo* butter acid extract; and
  (vi) separating the *kombo* butter acid extract by chromatography to obtain a compound selected from the group consisting of sargaquinoic acid (KB-1), sargachromenol (KB-2), and sargahydroquinoic acid (KB-3).

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound selected from sargaquinoic acid (KB-1), sargachromenol (KB-2), and sargahydroquinoic acid (KB-3), or a pharmaceutically acceptable salt, solvate, or prodrug thereof, wherein the compound is isolated from or a component of a chemical fraction of African nutmeg seeds, wherein the chemical fraction of African nutmeg seeds is a *kombo* butter acid extract prepared by a process comprising the steps of:
  (i) extracting the African nutmeg seeds with an aqueous alcohol solution to obtain an aqueous alcohol fraction and a first residue;
  (ii) separating the aqueous alcohol fraction from the first residue;
  (iii) washing the aqueous alcohol fraction with a first non-polar organic solvent;
  (iv) evaporating solvents from the washed aqueous alcohol fraction to obtain a crude *kombo* butter extract;
  (v) adding into the crude *kombo* butter extract an aqueous basic solution to obtain a solution of *kombo* butter acid salts and a second residue;
  (vi) separating the solution of *kombo* butter acid salts and the second residue;
  (vii) acidifying the solution of *kombo* butter acid salts to obtain a mixture containing *kombo* butter acids;
  (viii) extracting the mixture with a second non-polar organic solvent to obtain an aqueous fraction and an organic fraction;
  (ix) separating the aqueous fraction and the organic fraction; and
  (x) evaporating the solvent from the organic fraction to obtain the *kombo* butter acid extract,
  wherein the first non-polar organic solvent and the second non-polar organic solvent are the same or different.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound selected from sargaquinoic acid (KB-1), sargachromenol (KB-2), and sargahydroquinoic acid (KB-3), or a pharmaceutically acceptable salt, solvate, or prodrug thereof, wherein the compound is isolated from or a component of a chemical fraction of African nutmeg seeds, wherein the chemical fraction of African nutmeg seeds is a *kombo* butter acid extract prepared by a process comprising the steps of:
  (i) extracting the African nutmeg seeds with an aqueous alcohol solution to obtain an aqueous alcohol fraction and a first residue;
  (ii) separating the aqueous alcohol fraction from the first residue;
  (iii) washing the aqueous alcohol fraction with a first non-polar organic solvent;
  (iv) evaporating solvents from the washed aqueous alcohol fraction to obtain a crude *kombo* butter extract;
  (v) adding into the crude *kombo* butter extract an aqueous basic solution to obtain a solution of *kombo* butter acid salts and a second residue;
  (vi) separating the solution of *kombo* butter acid salts and the second residue;
  (vii) acidifying the solution of *kombo* butter acid salts to obtain a mixture containing *kombo* butter acids;
  (viii) extracting the mixture with a second non-polar organic solvent to obtain an aqueous fraction and an organic fraction;
  (ix) separating the aqueous fraction and the organic fraction;
  (x) evaporating the solvent from the organic fraction to obtain the *kombo* butter acid extract; and
  (xi) separating the *kombo* butter acid extract by chromatography to obtain a compound selected from the group consisting of sargaquinoic acid (KB-1), sargachromenol (KB-2), and sargahydroquinoic acid (KB-3).
  wherein the first non-polar organic solvent and the second non-polar organic solvent are the same or different.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the composition further comprises a pharmaceutically acceptable carrier.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the composition is co-administered with a second neuroprotective agent.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the neurodegenerative disease or disorder is a central nervous system (CNS) injury, stroke, paralysis, or cognitive memory deterioration.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the neurodegenerative disease or disorder is ischemic stroke.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the neurodegenerative disease or disorder is selected from Parkinson's disease, Alzheimer's disease, and Huntington's disease.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the subject is a mammalian animal.

In another embodiment of the first aspect, the present invention provides a method for preventing or treating a neurological or neurodegenerative disease or disorder, the method comprising administering to a subject suffering from the disease or disorder a composition comprising a therapeutically effective amount of a compound according to Formula (I), (II), or (III), or a pharmaceutically acceptable salt, solvate, or prodrug thereof, wherein the subject is a human.

In a second aspect the present invention provides a method for preventing or treating a neurological or neurodegenerative disease or disorder, the method comprising administering to a subject suffering from the disease or disorder a composition comprising a chemical fraction of African nutmeg seeds.

In one embodiment of the second aspect, the present invention provides a method for preventing or treating a neurological or neurodegenerative disease or disorder, the method comprising administering to a subject suffering from the disease or disorder a composition comprising a chemical fraction of African nutmeg seeds, wherein the chemical fraction of African nutmeg seeds is a *kombo* butter acid extract.

In one embodiment of the second aspect, the present invention provides a method for preventing or treating a neurological or neurodegenerative disease or disorder, the method comprising administering to a subject suffering from the disease or disorder a composition comprising a chemical fraction of African nutmeg seeds, wherein the composition further comprises an additional material selected from: (i) unprocessed, processed or partially processed nuts and/or seeds of African nutmeg; (ii) enriched extract of sargaquinoic acid (KB-1), sargachromenol (KB-2), and/or sargahydroquinoic acid (KB-3); and (iii) isolated sargaquinoic acid (KB-1), sargachromenol (KB-2), sargahydroquinoic acid (KB-3), or synthetic derivatives thereof.

In another embodiment of the second aspect, the present invention provides a method for preventing or treating a neurological or neurodegenerative disease or disorder, the method comprising administering to a subject suffering from the disease or disorder a composition comprising a chemical fraction of African nutmeg seeds, wherein the chemical fraction of African nutmeg seeds is a *kombo* butter acid extract prepared by a process comprising the steps of:
  (i) optionally milling the African nutmeg seeds to obtain a ground seed paste;
  (ii) extracting the African nutmeg seeds or the ground seed paste with an aqueous basic solution to obtain a solution of *kombo* butter acid salts and a residue;
  (iii) acidifying the solution of *kombo* butter acid salts to obtain a mixture of *kombo* butter acids;
  (iv) extracting the mixture of *kombo* butter acids with a non-polar organic solvent to obtain an aqueous fraction and an organic fraction; and
  (v) evaporating the solvent from the organic fraction to obtain the *kombo* butter acid extract.

In another embodiment of the second aspect, the present invention provides a method for preventing or treating a neurological or neurodegenerative disease or disorder, the method comprising administering to a subject suffering from the disease or disorder a composition comprising a chemical fraction of African nutmeg seeds, wherein the chemical fraction of African nutmeg seeds is a *kombo* butter acid extract prepared by a process comprising the steps of:
  (i) optionally milling the African nutmeg seeds to obtain a ground seed paste;
  (ii) extracting the African nutmeg seeds or the ground seed paste with an aqueous basic solution to obtain a solution of *kombo* butter acid salts and a residue;
  (iii) acidifying the solution of *kombo* butter acid salts to obtain a mixture of *kombo* butter acids;
  (iv) extracting the mixture of *kombo* butter acids with a non-polar organic solvent to obtain an aqueous fraction and an organic fraction;
  (v) evaporating the solvent from the organic fraction to obtain the *kombo* butter acid extract; and
  (vi) separating the *kombo* butter acid extract by chromatography to obtain a compound selected from the group consisting of sargaquinoic acid (KB-1), sargachromenol (KB-2), and sargahydroquinoic acid (KB-3).

In another embodiment of the second aspect, the present invention provides a method for preventing or treating a neurological or neurodegenerative disease or disorder, the method comprising administering to a subject suffering from the disease or disorder a composition comprising a chemical fraction of African nutmeg seeds, wherein the chemical fraction of African nutmeg seeds is a *kombo* butter acid extract prepared by a process comprising the steps of:

(i) extracting the African nutmeg seeds with an aqueous alcohol solution to obtain an aqueous alcohol fraction and a first residue;
(ii) separating the aqueous alcohol fraction from the first residue;
(iii) washing the aqueous alcohol fraction with a first non-polar organic solvent;
(iv) evaporating solvents from the washed aqueous alcohol fraction to obtain a crude *kombo* butter extract;
(v) adding into the crude *kombo* butter extract an aqueous basic solution to obtain a solution of *kombo* butter acid salts and a second residue;
(vi) separating the solution of *kombo* butter acid salts and the second residue;
(vii) acidifying the solution of *kombo* butter acid salts to obtain a mixture containing *kombo* butter acids;
(viii) extracting the mixture with a second non-polar organic solvent to obtain an aqueous fraction and an organic fraction;
(ix) separating the aqueous fraction and the organic fraction; and
(x) evaporating the solvent from the organic fraction to obtain the *kombo* butter acid extract, wherein the first non-polar organic solvent and the second non-polar organic solvent are the same or different.

In another embodiment of the second aspect, the present invention provides a method for preventing or treating a neurological or neurodegenerative disease or disorder, the method comprising administering to a subject suffering from the disease or disorder a composition comprising a chemical fraction of African nutmeg seeds, wherein the chemical fraction of African nutmeg seeds is a *kombo* butter acid extract prepared by a process comprising the steps of:
(i) extracting the African nutmeg seeds with an aqueous alcohol solution to obtain an aqueous alcohol fraction and a first residue;
(ii) separating the aqueous alcohol fraction from the first residue;
(iii) washing the aqueous alcohol fraction with a first non-polar organic solvent;
(iv) evaporating solvents from the washed aqueous alcohol fraction to obtain a crude *kombo* butter extract;
(v) adding into the crude *kombo* butter extract an aqueous basic solution to obtain a solution of *kombo* butter acid salts and a second residue;
(vi) separating the solution of *kombo* butter acid salts and the second residue;
(vii) acidifying the solution of *kombo* butter acid salts to obtain a mixture containing *kombo* butter acids;
(viii) extracting the mixture with a second non-polar organic solvent to obtain an aqueous fraction and an organic fraction;
(ix) separating the aqueous fraction and the organic fraction;
(x) evaporating the solvent from the organic fraction to obtain the *kombo* butter acid extract; and
(xi) separating the *kombo* butter acid extract by chromatography to obtain a compound selected from the group consisting of sargaquinoic acid (KB-1), sargachromenol (KB-2), and sargahydroquinoic acid (KB-3), wherein the first non-polar organic solvent and the second non-polar organic solvent are the same or different.

In a third aspect the present invention provides a compound of Formula (KB-2a) or (KB-3a):

or a pharmaceutically acceptable salt, solvent or prodrug thereof.

In one embodiment of the third aspect, the present invention provides a compound of Formula (KB-2a), namely 6-acetyl-sargachromenal, isolated from an acetylated mixture of *kombo* butter acid extract and purified by silica gel column chromatography.

In another embodiment of the third aspect, the present invention provides a compound of Formula (KB-3a), namely 1,4-diacetyl-sargahydroquinoic acid, isolated from an acetylated mixture of *kombo* butter acid extract and purified by silica gel column chromatography.

In another embodiment of the third aspect, the present invention provides a compound of Formula (KB-2a) or (KB-3a) isolated from an acetylated mixture of *kombo* butter acid extract, wherein the acetylated mixture of *kombo* butter acid extract is prepared by a process comprising the steps of:
(i) optionally milling the African nutmeg seeds to obtain a ground seed paste;
(ii) extracting the African nutmeg seeds or the ground seed paste with an aqueous basic solution to obtain a solution of *kombo* butter acid salts and a residue;

(iii) separating the solution of *kombo* butter acid salts and the residue;
(iv) acidifying the solution of *kombo* butter acid salts to obtain a mixture containing *kombo* butter acids;
(v) extracting the mixture with a non-polar organic solvent to obtain an aqueous fraction and an organic fraction;
(vi) separating the aqueous fraction and the organic fraction;
(vii) optionally evaporating the organic fraction to obtain the *kombo* butter acid extract and re-dissolving the crude extract in a second solvent; and
(viii) reacting the extract with acetyl chloride or acetic anhydride in the presence of a base.

In another embodiment of the third aspect, the present invention provides a compound of Formula (KB-2a) or (KB-3a) isolated from an acetylated mixture of *kombo* butter acid extract and prepared by a process comprising the steps of:
(i) optionally milling the African nutmeg seeds to obtain a ground seed paste;
(ii) extracting the African nutmeg seeds or the ground seed paste with an aqueous basic solution to obtain a solution of *kombo* butter acid salts and a residue;
(iii) separating the solution of *kombo* butter acid salts and the residue;
(iv) acidifying the solution of *kombo* butter acid salts to obtain a mixture containing *kombo* butter acids;
(v) extracting the mixture with a non-polar organic solvent to obtain an aqueous fraction and an organic fraction;
(vi) separating the aqueous fraction and the organic fraction;
(vii) optionally evaporating the organic fraction to obtain the *kombo* butter acid extract and re-dissolving the crude extract in a second solvent;
(viii) reacting the extract with acetyl chloride or acetic anhydride in the presence of a base; and
(ix) isolating the acetylated compound from the reaction mixture.

In another embodiment of the third aspect, the present invention provides a compound of Formula (KB-2a) or (KB-3a) prepared by a process comprising the steps of:
(i) optionally milling the African nutmeg seeds to obtain a ground seed paste;
(ii) extracting the African nutmeg seeds or the ground seed paste with an aqueous basic solution to obtain a solution of *kombo* butter acid salts and a residue;
(iii) separating the solution of *kombo* butter acid salts and the residue;
(iv) acidifying the solution of *kombo* butter acid salts to obtain a mixture containing *kombo* butter acids;
(v) extracting the mixture with a non-polar organic solvent to obtain an aqueous fraction and an organic fraction;
(vi) separating the aqueous fraction and the organic fraction;
(vii) optionally evaporating the organic fraction to obtain the *kombo* butter acid extract and re-dissolving the crude extract in a second solvent;
(viii) reacting the extract with acetyl chloride or acetic anhydride in the presence of a base;
(ix) isolating the acetylated compound from the reaction mixture; and
(x) purifying the isolated acetylated compound.

In another embodiment of the third aspect, the present invention provides a compound of Formula (KB-2a) or (KB-3a) isolated from an acetylated mixture of *kombo* butter acid extract, wherein the acetylated mixture of *kombo* butter acid extract is prepared by a process comprising the steps of:
(i) optionally milling the African nutmeg seeds to obtain a ground seed paste;
(ii) extracting the African nutmeg seeds or the ground seed paste with an aqueous basic solution to obtain a solution of *kombo* butter acid salts and a residue;
(iii) acidifying the solution of *kombo* butter acid salts to obtain a mixture of *kombo* butter acids;
(iv) extracting the mixture of *kombo* butter acids with a non-polar organic solvent to obtain an aqueous fraction and an organic fraction;
(v) optionally evaporating the solvent from the organic fraction to obtain the *kombo* butter acid extract; and
(vi) reacting the extract with acetyl chloride or acetic anhydride in the presence of a base.

In another embodiment of the third aspect, the present invention provides a compound of Formula (KB-2a) or (KB-3a) isolated from an acetylated mixture of *kombo* butter acid extract and prepared by a process comprising the steps of:
(i) optionally milling the African nutmeg seeds to obtain a ground seed paste;
(ii) extracting the African nutmeg seeds or the ground seed paste with an aqueous basic solution to obtain a solution of *kombo* butter acid salts and a residue;
(iii) acidifying the solution of *kombo* butter acid salts to obtain a mixture of *kombo* butter acids;
(iv) extracting the mixture of *kombo* butter acids with a non-polar organic solvent to obtain an aqueous fraction and an organic fraction;
(v) optionally evaporating the solvent from the organic fraction to obtain the *kombo* butter acid extract;
(vi) reacting the extract with acetyl chloride or acetic anhydride in the presence of a base; and
(vii) isolating the acetylated compound from the reaction mixture.

In another embodiment of the third aspect, the present invention provides a compound of Formula (KB-2a) or (KB-3a) prepared by a process comprising the steps of:
(i) optionally milling the African nutmeg seeds to obtain a ground seed paste;
(ii) extracting the African nutmeg seeds or the ground seed paste with an aqueous basic solution to obtain a solution of *kombo* butter acid salts and a residue;
(iii) acidifying the solution of *kombo* butter acid salts to obtain a mixture of *kombo* butter acids;
(iv) extracting the mixture of *kombo* butter acids with a non-polar organic solvent to obtain an aqueous fraction and an organic fraction;
(v) optionally evaporating the solvent from the organic fraction to obtain the *kombo* butter acid extract;
(vi) reacting the extract with acetyl chloride or acetic anhydride in the presence of a base;
(vii) isolating the acetylated compound from the reaction mixture; and
(viii) purifying the isolated acetylated compound In another embodiment of the third aspect, the present invention provides a composition comprising a compound of Formula (KB-2a) or (KB-3a), or a pharmaceutically acceptable salt, solvate, or prodrug thereof.

In another embodiment of the third aspect, the present invention provides a composition comprising a compound of Formula (KB-2a) or (KB-3a), or a pharmaceutically acceptable salt, solvate, or prodrug thereof, and a pharmaceutically acceptable carrier.

In another embodiment of the third aspect, the present invention provides a method for preventing or treating a neurological or neurodegenerative disease or disorder, the method comprising administering to a subject suffering from the disease or disorder a therapeutically effective amount of the compound of Formula (KB-2a) or (KB-3a) or a composition comprising a compound of Formula (KB-2a) or (KB-3a).

DEFINITIONS

Definitions have been provided above for each of the groups defined. In addition, the following definitions shall be used.

As used herein, the singular forms "a", "an", and "the" include plural reference unless the context clearly dictates otherwise.

The term "acetyl," as used herein, refers to —C(O)CH$_3$.

The term "alkoxy," as used herein, refers to an alkyl group attached to the parent molecular moiety through an oxygen atom. Representative examples of alkoxy group include, but are not limited to, methoxy, ethoxy, and tert-butoxy.

The term "alkyl," as used herein, refers to a group derived from a straight or branched chain saturated hydrocarbon by removal of a hydrogen from one of the saturated carbons. Representative examples of alkyl group include, but are not limited to, methyl, ethyl, isopropyl, and tert-butyl.

The term "aryl," as used herein, refers to a group derived from an aromatic carbocycle by removal of a hydrogen atom from an aromatic ring. Representative examples of aryl groups include, but are not limited to, phenyl and naphthyl.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by at least one halogen atom. The haloalkyl group can be an alkyl group of which all hydrogen atoms are substituted by halogens. Representative examples of haloalkyl include, but are not limited to, trifluoromethyl (CF$_3$—), 1-chloroethyl (ClCH$_2$CH$_2$—), and 2,2,2-trifluoroethyl (CF$_3$CH$_2$—).

The term "heteroaryl," as used herein, refers to group derived from a monocyclic or bicyclic aromatic compound comprising one or more heteroatoms, preferably, one to three heteroatoms, independently selected from nitrogen, oxygen, and sulfur, by removal of a hydrogen atom from an aromatic ring thereof. As is well known to those skilled in the art, heteroaryl rings have less aromatic character than their all-carbon counterparts. Thus, for the purpose of the invention, a heteroaryl group need only have some degree of aromatic character. Illustrative examples of heteroaryl groups include, but are not limited to, pyridyl, pyrimidinyl, furyl, thienyl, isoxazolyl, thiazolyl, quinolinyl, and isoquinolinyl.

The terms "hydroxy" or "hydroxyl," as used herein, refer to —OH.

The term "solvate," as used herein, refers to a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

The compounds of the present disclosure can exist as pharmaceutically acceptable salts. Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound, as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of subject compounds or pharmaceutically acceptable salts thereof, and one or more pharmaceutically acceptable carriers, diluents, or excipients.

In addition, compounds encompassed by the present invention may have prodrug forms. Any compound that will be converted in vivo to provide the bioactive agent is a prodrug within the scope of the invention. Various forms of prodrugs are well known in the art. For examples of such prodrug derivatives, see *Design of Prodrugs*, edited by H. Bundgaard (Elsevier, 1985), and *Methods in Enzymology*, Vol. 112, at pp. 309-396, edited by K. Widder et al. (Academic Press, 1985); and *A Textbook of Drug Design and Development*, edited by Krosgaard-Larsen and H. Bundgaard, Chapter 5, "*Design and Application of Prodrugs*," by H. Bundgaard, at pp. 113-191 (1991).

Compounds containing a carboxy or hydroxyl group, such as the compounds disclosed in the present invention, can form physiologically hydrolyzable esters that serve as prodrugs by being hydrolyzed in the body to yield the parent compounds. Thus, the present invention encompasses use of sargaquinoic acid (KB-1), sargachromenol (KB-2), and sargahydroquinoic acid (KB-3), and their ester derivatives as neuroprotective agents. The esters can occur at the carboxyl group of these compounds, including but not limited to the methyl ester, ethyl ester, or other long-chain alkyl esters. The esters can also occur at the hydroxyl group(s) of KB-2 and KB-3, including but not limited to those derived from acylation of the hydroxyl group(s) with, for example, acetic anhydride, butyryl chloride, succinic anhydride, nicotinyl chloride, or their equivalents. Such prodrugs are preferably administered orally since hydrolysis in many instances occurs principally under the influence of the digestive enzymes. Parenteral administration may be used where the ester per se is active, or in those instances where hydrolysis occurs in the blood. Such esters may be prepared by conventional techniques known in the art.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The carrier(s), diluent (s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a subject compound, or a pharmaceutically acceptable salt thereof, with one or more pharmaceutically acceptable carriers, diluents, or excipients.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Pharmaceutical formulations adapted for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

EXAMPLES

The invention is described more fully by way of the following non-limiting examples. All references cited herein are incorporated by reference in their entirety herein.

Example 1

Preparation of *Kombo* Butter from African Nutmeg Seeds

As described in the patent by Simon et al. (U.S. Pat. No. 7,371,413) *Kombo* butter was prepared from African nutmeg seeds (also referred to as *kombo* seeds) by several methods including, but not limited to, aqueous extraction, non-polar solvent extraction, and mechanical pressing. The yield of *kombo* butter obtained via these extraction procedures was generally in the range of 33-60% by weight of the starting material. An appreciable amount of yield loss (10-15%) resulted from oil retention in the filtration step. African nutmeg seeds were harvested and washed thoroughly with water. The clean seeds were dried and ground into a fine paste using a mechanical mill Three extraction methods were then alternately applied to the *kombo* seeds to recover the *kombo* seed oil, otherwise known as *kombo* butter.

During aqueous extraction, excess water (approximately twice the paste volume) was added to the ground paste and brought to a boil in large open pans for several hours as oil rose to the surface of the liquid. The emerging oil phase was intermittently skimmed off the top of the boiling liquid into a separate receiving container until the oil was depleted from the boiling extract. The oil collected was passed through cheesecloth filters while hot to remove any debris from the oil extract. The filtered oil was then allowed to cool and solidify into a reddish-brown butter.

During solvent extraction, petroleum ether was added to the ground paste and extraction was allowed to proceed for several minutes. The ether extract was decanted from the solid residue and then filtered. Upon evaporation of the solvent, the reddish-brown butter was obtained.

To process multi-kilogram quantities of *kombo* butter, the ground paste was subjected to mechanical pressure in an oilseed press to separate the oil from the solid residue. The mechanical press employed was identical to screw presses commonly used for processing oil palm and shea butter. The oil was then filtered into a collecting vessel. Since *kombo* butter is highly viscoelastic and tends to solidify quickly, it was necessary to supply heat via steam heat exchangers to maintain the oil in a free-flowing state during filtration of the butter.

Example 2

Preparation of *Kombo* Butter Acid Extracts

As described in the patent by Simon et al. (U.S. Pat. No. 7,371,413) *Kombo* butter acid extracts can be prepared from the *kombo* butter obtained as previously described. First, the *kombo* butter is extracted using 70-100% ethanol:water, preferably 95% ethanol:water. When we subjected *kombo* butter to extraction with 95% ethanol:water, we obtained a reddish-brown solution separately from an insoluble fraction that solidified to a pale-yellow fat. When we evaporated the reddish-brown solution, we obtained a crude *kombo* butter extract, a reddish-brown liquid that amounted to approximately 37% by weight of the *kombo* butter. The reddish-brown solution containing the crude extract in 70-100% ethanol:water is then extracted with a non-polar organic solvent such as petroleum ether, hexane, or chloroform, preferably petroleum ether. Upon evaporation of the ethanolic layer, the residue is washed with dilute aqueous base, preferably 5-30% NaOH solution, at which point the *kombo* butter acids are mainly present as their respective salts in aqueous solution. The *kombo* butter acids are recovered by acidifying the solution with an inorganic acid and extracting the acidified solution with a non-polar organic solvent such as petroleum ether, hexane, or chloroform. Upon evaporation of the organic solvent fraction, a *kombo* butter acid extract is obtained which typically contains 0.5-2% sargaquinoic acid (KB-1), 5-10% sargachromenol (KB-2), and 30-50% sargahydroquinoic acid (KB-3) with a reddish-brown liquid (KB-3).

We have also obtained *kombo* butter acid extracts directly from the ground paste of *kombo* seeds without first preparing *kombo* butter via direct extraction of the ground paste with 70-100% ethanol:water. Direct extraction of the ground paste with 95% ethanol followed by the addition of petroleum ether provides two separate phases. The ethanol layer is decanted and evaporated to yield a viscous reddish-brown liquid constituting 20% by weight of the ground paste. Evaporation of the petroleum ether layer yields a pale-yellow solid fat constituting 36% by weight of the ground paste. We have discovered that the viscous reddish-brown liquid obtained from the ethanol layer dissolves readily in dilute aqueous base, preferably 5-30% NaOH, more preferably 10% NaOH, whereas the pale-yellow solid fat is much less soluble, giving a cloudy solution that lathers with vigorous shaking. The solubility difference between these two fractions presents a second means for the isolation of a *kombo* butter acid extract directly from the *kombo* seeds without prior preparation of *kombo* butter. Accordingly, we have also developed a simple method for the separation of *kombo* butter acids from the ground paste of *kombo* seeds as an aqueous extract prior to oil extraction.

The *kombo* butter acids can then be reclaimed from the solution of aqueous base by acidification and subsequent extraction with a non-polar solvent as previously described herein.

Example 3

Preparation of Acetylated Derivatives of *Kombo* Butter Acid Extracts

New here in this discovery and patent claim is in the preparation of acetylated derivatives of *Kombo* butter acid extracts to improve stability and to provide additional novel compounds with similar activity. As the KB fractions can be unstable, *Kombo* butter acid extract (2.1 g) was dissolved in 40 ml of methylene chloride and sonicated for 10 min, and then cooled down with a ice/water bath for 5 min. We then added pyridine $C_5H_5N$ (6×mol), 4-(dimethylamino) pyridine (3×mol) and acetic anhydride (3×mol), and stirred/mixed the reaction mixture overnight at room temperature. Water was added to quench the reaction (5 ml per gram of extract) and separate the organic layer. The organic layer was then washed with acid to remove the pyridine, then with water and brine to remove the acid. The treated organic layer was then dried and concentrated to give 1.1 g derivative mixture of *Kombo* butter acid extract.

Example 4

Purification of Major Components Sargaquinoic Acid (KB-1), Sargachromenol (KB-2), and Sargahydroquinoic Acid (KB-3) from *Kombo* Butter Acid Extracts Using various chromatographic methods on silica gel and Sephadex LH-20, as well as reversed phase preparative HPLC under monitoring of thin layer chromatography (TLC) and LC/MS, we purified 3 major components compounds sargaquinoic acid (KB-1), sargachromenol (KB-2), and sargahydroquinoic acid (KB-3) from the *kombo* butter acid extracts prepared as previously described. The structures of these compounds were elucidated by MS, $^1$H-NMR, $^{13}$C-NMR, and 2D-NMR ($^1$H-$^1$H COSY, HMBC and HMQC) and confirmed their identities as sargaquinoic acid, sargachromenol, and sargahydroquinoic acid by comparison with known spectra. According to our 2D-NMR data, we determined that the major constituent of *kombo* butter is sargahydroquinoic acid, not kombic acid as reported earlier. (Perez-Castorena, A. L., et al., *Planta Medica* 68(7):645-7 (2002)).

*Kombo* butter acid extract (~3 g) was chromatographed on a silica gel column (200 g, 130-270 mesh) and eluted by hexane-ethyl acetate (with 0.1% acetic acid as modifier) in gradient. A total of 3 subfractions were collected based on the TLC and LC/MS results. Subfraction 1 was further subjected to Sephadex LH-20 gel filtration chromatography using methanol as eluent. The major component was further purified by preparative HPLC on a Varian Dynamax 150×41.1 mm, Microsob 60-8 C18 column using acetonitrile and water (with 0.1% acetic acid as modifier) as eluent in gradient at a flow rate 20 ml/minute to obtain 48.9 mg of pure sargaquinoic acid, also referred to herein as compound KB-1.

Subfraction 2 was further subjected to Sephadex LH-20 gel filtration chromatography using methanol as eluent. Subsequently, the major component was further purified by preparative HPLC on a Varian Dynamax 150×41.1 mm, Microsob 60-8 C18 column with acetonitrile and water (with 0.1% acetic acid as modifier) as eluent in gradient at a flow rate 20 ml/minute to obtain 148.3 mg of pure sargachromenol, also referred to herein as compound KB-2.

Subfraction 3 was further subjected to Sephadex LH-20 gel filtration chromatography using methanol as eluent. Subsequently, the major component was further purified by preparative HPLC on a Varian Dynamax 150×41.1 mm, Microsob 60-8 C18 column with acetonitrile and water (with 0.1% acetic acid as modifier) as eluent in gradient at a flow rate 20 ml/minute to obtain 645.4 mg of pure sargahydroquinoic acid, also referred to herein as compound KB-3.

Example 5

Purification of Major Components 6-Acetyl-sargachromenol (KB-2a), and 1,4,-Diacetyl-sargahydroquinoic acid (KB-3a) from Acetylated Derivatives of *Kombo* Butter Acid Extracts Using a combination of chromatographic methods on silica gel and Sephadex LH-20, as well as reversed phase preparative HPLC under monitoring of thin layer chromatography (TLC) and LC/MS, in purified 2 major components compounds 6-acetyl-sargachromenol (KB-2a), and 1,4,-diacetyl-sargahydroquinoic acid (KB-3a) from acetylated derivatives of *Kombo* butter acid extracts prepared as previously described. The structures of these compounds were elucidated by MS, $^1$H-NMR and $^{13}$C-NMR data.

Acetylated mixture of *Kombo* butter acid extract (~3 g) was directly uploaded on a silica gel column (200 g, 130-270 mesh) and eluted by hexane-ethyl acetate (with 0.1% acetic acid as modifier) in gradient. A total of 3 subfractions were collected based on the TLC and LC/MS results. Subfraction 1 was further subjected to Sephadex LH-20 gel filtration chromatography using methanol as eluent. The major component was further purified by preparative HPLC on a Varian Dynamax 150×41.1 mm, Microsob 60-8 C18 column using acetonitrile and water (with 0.1% acetic acid as modifier) as eluent in gradient at a flow rate 20 ml/minute to obtain 43.2 mg of pure 6-acetyl-sargachromenol, also referred to herein as compound KB-2a.

Subfraction 2 showing one major peak was further purified by preparative HPLC on a Varian Dynamax 150×41.1 mm, Microsob 60-8 C18 column with acetonitrile and water (with 0.1% acetic acid as modifier) as eluent in gradient at a flow rate 20 ml/minute to obtain 496.0 mg of pure 1,4,-diacetyl-sargahydroquinoic acid, also referred to herein as compound KB-3a.

Example 6

Figure 3:
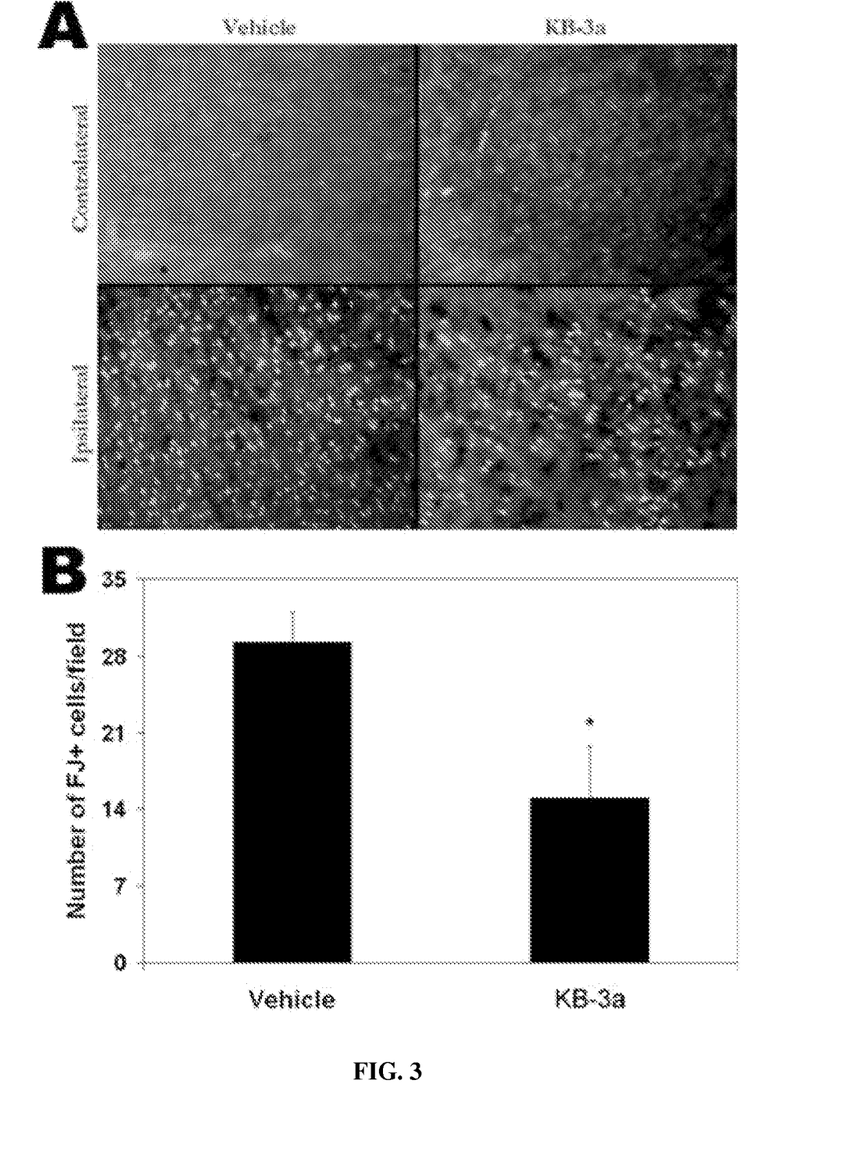
FIG. 3 depicts the effect of KB-3a treatment on Fluoro-Jade B stained degenerating neurons following pMCAO. Vehicle or 30 mg/kg KB-3a was administered 2 hr before and 6 hr after pMCAO. (A) Fluoro-Jade B stained ipsilateral cortical sections showing KB-3a protection against ischemic neuronal damage. (B) Quantitative analysis of Fluoro-Jade B staining within the ipsilateral cortex in mice treated with KB-3a (*, $p<0.05$).
Figure 4:
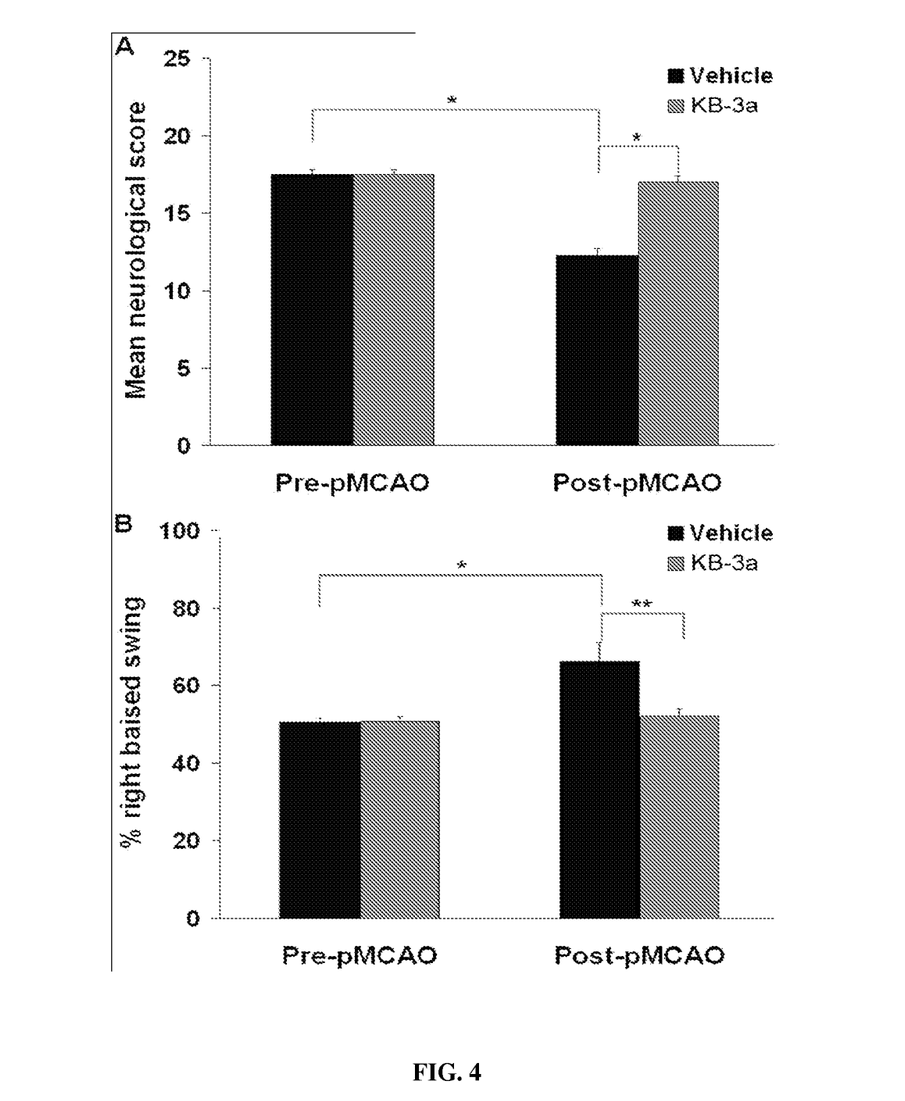

Bioactivities of the *Kombo* Butter Preparation and Constituents Derived from *Kombo* Butter We determined the neuroprotective activity of *kombo* butter and *kombo* butter acid extract, which is enriched in KB1, KB-2 and KB-3, as well as the three major pure compounds, sargaquinoic acid (KB-1), sargachromenol (KB-2), and sargahydroquinoic acid (KB-3), and the derivatives. Specifically, the adult pMCAO mice (permanent middle cerebral artery occlusion) treated with the preparations and compounds was investigated and showed significant reduction in the brain infarct volume (FIG. 1 and FIG. 2) and degenerating neurons (FIG. 3) compared with the vehicle-treated control group. To determine whether the induced reduction in infarct volume and neuronal damage could translate into functional recovery, neurological evaluations were performed. The results showed that the mice treated with the preparations and compounds exhibited a significant improvement in neurological performance (FIG. 4).

Example 7

Figure 1:
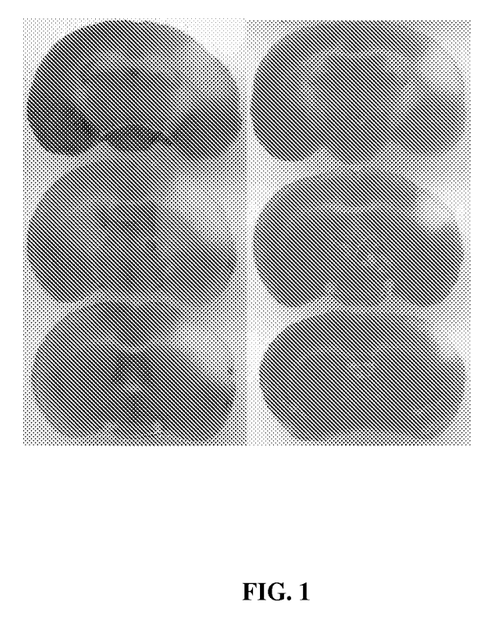
FIG. 1 contains representative photographs of tetrazolium chloride (TTC) stained coronal brain slices of mice 24 hrs after pMCAO showing "red" (darkened area) staining of normal brain tissue and "white" non-stained infarct area. Left Panel: vehicle-treated; Right Panel: treated by KB-3a (30 mg/kg).
Figure 2:
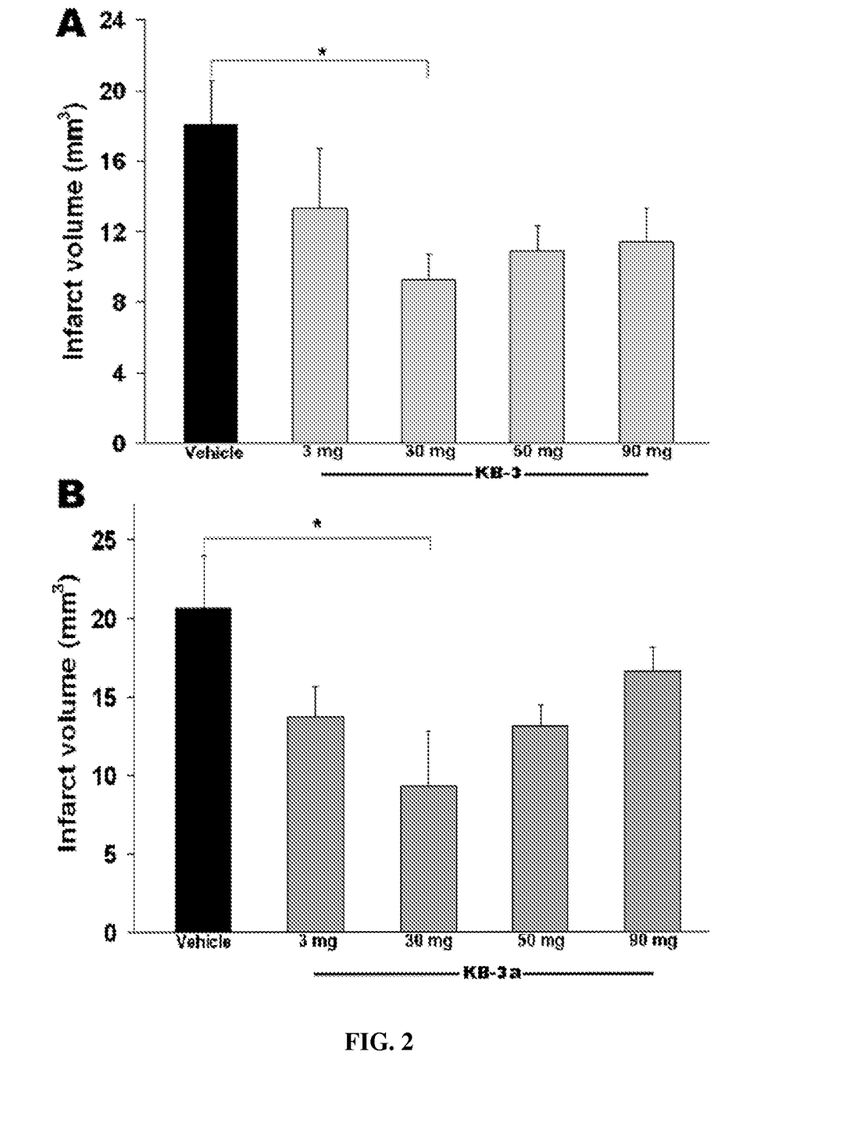
FIG. 2 depicts the effect of various doses of KB-3 (A) or KB-3a (B) on infarct volume in mice 24 hrs following pMCAO. KB-3 or KB-3a was administered at 2 hr before and 6 hr after pMCAO. Histogram values represent mean±SEM (*, $p<0.04$).

Triphenyltetrazolium Chloride (TTC) Staining to Determine Infarct Volume Shows that KB-3 or KB-3a Treatment Confers Neuroprotection Against pMCAO Human stroke typically involves disruption of blood flow to a specific region supplied often by the middle cerebral artery (MCA). The classical animal model of focal ischemia, MCA occlusion (MCAO), produces the problem of long-term vessel blockade, simulating what often occurs in human stroke. We have induced focal cerebral ischemia in mice by cauterizing the MCA. To evaluate the acute injury induced by MCAO, animals were euthanized at 24 h after MCAO, and the infarct volume was determined using 2,3,5-triphenyltetrazolium chloride (TTC) staining. (Rajanikant, G. K., et al., *Stroke*, 38:3023-31 (2007)). In brief, 24 hours after pMCAO, animals were deeply anesthetized with an injection of pentobarbital (70 mg/kg, i.p.) and subjected to intracardiac perfusion with 100 mL of isotonic saline delivered through an electronic pump at 100 mm Hg. The head was then removed with a small animal guillotine and the brain carefully dissected out en bloc. After a brief (<1 minute) period of cooling on a bed of ice, the brain was sliced coronally at 1-mm intervals. Individual slices were freed from dura mater and vascular tissue and soaked for 10 minutes in a solution of 2% TTC in 0.1 mol/L PBS (pH adjusted to 7.4), warmed to 37° C. in a water bath. Gentle stirring of the slices ensured even exposure of the surfaces to staining. Excess TTC was then drained, and slices were refrigerated in 10% formalin. Scanned images of the stained slices were then generated. FIG. 1 shows the representative photographs of TTC stained coronal brain slices 24 h after pMCAO with "red" staining of normal brain tissue and "white" non-stained infarct area. The infarct area was then quantified from the scanned images using the NIH Image J analysis software (version 1.38). The infarct volume in each slice was calculated by taking the average of the infarct area on both sides of the slice and multiplying it by the section thickness (1 mm) FIG. 2 shows the effect of KB-3 or KB-3a on infarct volume in mice 24 hr following pMCAO. Vehicle or various doses (3, 30, 50 or 90 mg/kg) of KB-3 or KB-3a were administered intraperitoneally 2 hr before and 6 hr after pMCAO and the infarct volume was measured at 24 hr post-pMCAO by TTC staining. Histogram values represent mean±SEM. The infarct volume in animals treated with KB-3 at 30 mg/kg was significantly smaller than in the vehicle-treated group (approximately 48% reduction; p<0.05, ANOVA with Tukey post-hoc test). In a separate set of experiment, ischemic mice were treated with KB-3a, the more stable acetylated derivative of KB-3 (prodrug). Significant reduction in infarct volume was achieved with KB-3a at 30 mg/kg, with approximately 54% reduction compared with the vehicle-treated control group (p<0.04, ANOVA with Tukey post-hoc test).

Example 8

Fluoro Jade B Staining to Determine Degenerating Neurons After pMCAO

We used brain coronal sections (30 µM) for Fluoro Jade B staining to determine degenerating neurons, as previously described. (Rajanikant, G. K., et al., *Stroke,* 38:3023-31 (2007)). In brief, the brain sections on glass slides were dried overnight, immersed for 3 min in 100% ethanol, for 1 min in 70% ethanol, and for 1 min in distilled water, and then incubated in a solution containing 0.01% Fluoro-Jade B (Histo-Chem Inc., Jefferson, Ark.) and 0.1% acetic acid (1:10) for 30 min on a shaker. After three 10-min washes, the slides were coverslipped, and labeled sections were visualized with a confocal laser-scanning microscope. FIG. 3 shows the Fluoro Jade B staining for degenerating neurons 24 h after MCAO in mice. KB-3a is protective against ischemic neuronal degeneration, and quantitative analysis of Fluoro-Jade B staining within the ipsilateral cortex in mice treated with KB-3a shows approximately 50% reduction as compared to the vehicle control (p<0.05).

Example 9

KB-3a Treatment Improves pMCAO-Induced Neurological Deficits

To determine whether KB-3a-induced reduction in infarct volume and neuronal degeneration could translate into functional recovery, neurological evaluations were performed right before the surgery and 24 hr following pMCAO. The neurobehavioral deficit scoring system consists of six tests as previously described in detail, which include: (1) spontaneous activity, (2) symmetry of four limb movement, (3) forepaw outstretching while held by tail, (4) climbing wall of wire cage, (5) reaction to touch on either side of trunk, and (6) response to vibrissae touch. (See Garcia, J. H., et al., *Stroke,* 26:627-34 (1995)). The neurological score given to each mouse at the completion of the evaluation is the summation of all six individual test scores. The minimum neurological score is 3 and the maximum is 18. Using the 18 point-based scale, the normal mean preoperative neurological score was 17.5±0.29. As shown in FIG. 4A, following pMCAO, vehicle-treated mice exhibited a statistically significant decrease in their neurological scores (12.3±0.48; p<0.01). However, the mice treated with 30 mg/kg KB-3a, exhibited a significant improvement in neurological performance at 24 hr post-pMCAO (17±0.41; p<0.01).

In addition, the elevated body-swing test (EBST), described in detail by Borlongan et al, was used by us to assess asymmetric motor behavior. (Borlongan, C. V. and Sanberg, P. R., *J. Neurosci.,* 15:5372-8 (1995)). Mice were held by the base of the tail and elevated about 10 cm from the tabletop. The direction of body swing, defined as an upper body turn of >10° to either side, was recorded for 1 min during each of three trials. The number of left and right turns was counted, and the percentage of turns made to the side contralateral to the ipsilateral hemisphere (% right-biased swing) was determined. (Ishibashi, S., et al., *Exp. Neurol.,* 207:302-13 (2007)). The EBST was used to detect asymmetry in motor behavior at 24 hr post-pMCAO. Post-ischemic vehicle treated animals showed a strong tendency to turn their upper body to the side contralateral to the stroked hemisphere, whereas pre-operated controls showed no bias. As shown in FIG. 4B, the percent right-biased swing was significantly higher in post-ischemic animals (66.4±4.9, p<0.01) than in pre-operated controls (50.55±1.05). Mice intraperitoneally treated with KB-3a at 2 hr pre- and 6 hr post-pMCAO, exhibited significantly less body asymmetry 24 hr after cerebral ischemia compared with the vehicle treated controls (52.16±1.8, p<0.02).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A method for treating a neurological or neurodegenerative disease or disorder, the method comprising administering to a subject suffering from the disease or disorder a composition comprising a therapeutically effective amount of a compound according to Formula (I), (II), or (III) as a neuroprotective agent:

or a pharmaceutically acceptable salt or solvate thereof, wherein:
$R^1$, at each occurrence, is independently hydrogen or $C_{1-6}$ alkyl;
$R^2$, $R^3$, and $R^4$ are each independently hydrogen or $R^5C(O)$—;
$R^5$ is selected from $C_{1-6}$ alkyl, $C_{6-10}$ aryl, or 5- to 10-membered heteroaryl, wherein the alkyl is optionally substituted by one, two, or three substituents independently selected from hydroxyl, halo, $C_{1-4}$ alkoxy, and —$CO_2R^6$, and wherein the aryl or heteroaryl is each optionally substituted by one to five substituents independently selected from $C_{1-4}$ alkyl, hydroxyl, halo, $C_{1-4}$ alkoxy, and —$CO_2R^6$; and
$R^6$ is hydrogen or $C_{1-4}$ alkyl; and
wherein the neurodegenerative disease or disorder is stroke, paralysis, or cognitive memory deterioration.

2. The method of claim 1, wherein $R^5$ is $C_{1-4}$ alkyl, $HO_2CCH_2CH_2$—, phenyl, or 3-pyridinyl.

3. The method of claim 1, wherein $R^1$ is each hydrogen and $R^2$, $R^3$, and $R^4$ are each $CH_3C(O)$—.

4. The method of claim 1, wherein $R^1$, $R^2$, $R^3$, and $R^4$ are each a hydrogen atom and wherein Formulas (I), (II), and (III) represent sargaquinoic acid (KB-1), sargachromenol (KB-2), and sargahydroquinoic acid (KB-3), respectively.

5. The method of claim 4, wherein the sargaquinoic acid, sargachromenol, and sargahydroquinoic acid are each a component of a chemical fraction of African nutmeg seeds, also known as *kombo* from the plant, *Pycnanthus angolensis*.

6. The method of claim 5, wherein the chemical fraction of African nutmeg seeds is a *kombo* butter acid extract prepared by a process comprising the steps of:
   (i) optionally milling the African nutmeg seeds to obtain a ground seed paste;
   (ii) extracting the African nutmeg seeds or the ground seed paste with an aqueous basic solution to obtain a solution of *kombo* butter acid salts and a residue;
   (iii) acidifying the solution of *kombo* butter acid salts to obtain a mixture of *kombo* butter acids;
   (iv) extracting the mixture of *kombo* butter acids with a non-polar organic solvent to obtain an aqueous fraction and an organic fraction; and
   (v) evaporating the solvent from the organic fraction to obtain the *kombo* butter acid extract.

7. The method of claim 6, wherein the process further comprises (vi) separating the *kombo* butter acid extract by chromatography to obtain a compound selected from the group consisting of sargaquinoic acid (KB-1), sargachromenol (KB-2), and sargahydroquinoic acid (KB-3).

8. The method of claim 5, wherein the chemical fraction of African nutmeg seeds is a *kombo* butter acid extract prepared by a process comprising the steps of:
   (i) extracting the African nutmeg seeds with an aqueous alcohol solution to obtain an aqueous alcohol fraction and a first residue;
   (ii) separating the aqueous alcohol fraction from the first residue;
   (iii) washing the aqueous alcohol fraction with a first non-polar organic solvent;
   (iv) evaporating solvents from the washed aqueous alcohol fraction to obtain a crude *kombo* butter extract;
   (v) adding into the crude *kombo* butter extract an aqueous basic solution to obtain a solution of *kombo* butter acid salts and a second residue;
   (vi) separating the solution of *kombo* butter acid salts and the second residue;
   (vii) acidifying the solution of *kombo* butter acid salts to obtain a mixture containing *kombo* butter acids;
   (viii) extracting the mixture with a second non-polar organic solvent to obtain an aqueous fraction and an organic fraction;
   (ix) separating the aqueous fraction and the organic fraction; and
   (x) evaporating the solvent from the organic fraction to obtain the *kombo* butter acid extract,
   wherein the first non-polar organic solvent and the second non-polar organic solvent are the same or different.

9. The method of claim 8, wherein the process further comprises (xi) separating the *kombo* butter acid extract by chromatography to obtain a compound selected from the group consisting of sargaquinoic acid (KB-1), sargachromenol (KB-2), and sargahydroquinoic acid (KB-3).

10. The method according to claim 1, wherein the composition further comprises a pharmaceutically acceptable carrier.

11. The method according to claim 1, wherein the composition is co-administered with a second neuroprotective agent.

12. The method according to claim 1, wherein the neurodegenerative disease or disorder is ischemic stroke.

13. The method according to claim 1, wherein the subject is a mammalian animal.

14. The method according to claim 1, wherein the subject is a human.

15. The method according to claim 1, wherein the composition is administered in an oral, parenteral, topical, or nasal route each independently in a form of solid, liquid, cream, spray, or inhalant.

* * * * *